(12) United States Patent
Vedamoorthy

(10) Patent No.: US 10,550,178 B2
(45) Date of Patent: Feb. 4, 2020

(54) ANTIBODIES FOR DETECTING REDOX MODULATED PROTEINS

(71) Applicant: Srikanth Vedamoorthy, Concord, NC (US)

(72) Inventor: Srikanth Vedamoorthy, Concord, NC (US)

(*) Notice: Subject to any disclaimer, the term of this patent is extended or adjusted under 35 U.S.C. 154(b) by 0 days.

(21) Appl. No.: 16/117,700

(22) Filed: Aug. 30, 2018

(65) Prior Publication Data

US 2018/0371070 A1 Dec. 27, 2018

Related U.S. Application Data

(63) Continuation-in-part of application No. 14/753,759, filed on Jun. 29, 2015, now Pat. No. 10,066,006, which is a continuation of application No. 13/051,425, filed on Mar. 18, 2011, now Pat. No. 9,067,982.

(60) Provisional application No. 61/340,458, filed on Mar. 18, 2010.

(51) Int. Cl.
| | |
|---|---|
| *A61K 39/395* | (2006.01) |
| *C12N 5/07* | (2010.01) |
| *C12N 5/16* | (2006.01) |
| *C12N 9/02* | (2006.01) |
| *C07K 16/00* | (2006.01) |
| *C12P 21/08* | (2006.01) |
| *C07K 16/18* | (2006.01) |
| *C12N 9/96* | (2006.01) |
| *C12N 9/99* | (2006.01) |
| *C12N 9/00* | (2006.01) |
| *C12N 9/04* | (2006.01) |
| *C12P 21/00* | (2006.01) |
| *C12P 21/02* | (2006.01) |
| *A61K 38/00* | (2006.01) |
| *C07K 16/44* | (2006.01) |
| *A61K 39/00* | (2006.01) |

(52) U.S. Cl.
CPC .......... *C07K 16/18* (2013.01); *C12N 5/163* (2013.01); *C12N 9/0002* (2013.01); *C12N 9/0006* (2013.01); *C12N 9/93* (2013.01); *C12N 9/96* (2013.01); *C12N 9/99* (2013.01); *C12P 21/00* (2013.01); *A61K 38/00* (2013.01); *A61K 2039/505* (2013.01); *A61K 2123/00* (2013.01); *C07K 16/44* (2013.01); *C07K 2319/00* (2013.01); *C12P 21/02* (2013.01)

(58) Field of Classification Search
CPC ................ C07K 16/00; A61K 2039/505
See application file for complete search history.

(56) References Cited

U.S. PATENT DOCUMENTS

| | | | |
|---|---|---|---|
| 4,179,337 A | 12/1979 | Davis et al. | |
| 9,067,982 B2 | 6/2015 | Vedamoorthy | |
| 10,066,006 B2 | 9/2018 | Vedamoorthy | |
| 2004/0096881 A1* | 5/2004 | Blasko ........... | C12Y 114/13039 435/6.14 |
| 2004/0105853 A1 | 6/2004 | Xiao | |

OTHER PUBLICATIONS

Caballero-Alia et al., Calcif Tissue Int, 2004; 75: 78-84. (Year: 2004).*
Findlay, Victoria J., et al. "A novel role for human sulfiredoxin in the reversal of glutathionylation." Cancer research 66.13 (2006): 6800-6806.
Gao, Xing-Huang, et al. "Methods for analysis of protein glutathionylation and their application to photosynthetic organisms." Molecular plant 2.2 (2009): 218-235.
Johansson, Magnus, and Mathias Lundberg. "Glutathionylation of beta-actin via a cysteinyl sulfenic acid intermediary." BMC biochemistry 8.1 (2007).
Wang, Jun, et al. "Stable and controllable RNA interference: Investigating the physiological function of glutathionylated actin." Proceedings of the National Academy of Sciences 100.9 (2003): 5103-5106.
Chintalacharuvu, Koteswara R., et al. "Hybrid IgA2/IgG1 antibodies with tailor-made effector functions." Clinical immunology 101.1 (2001): 21-31.
Frigerio, Lorenzo, et al. "Assembly, secretion, and vacuolar delivery of a hybrid immunoglobulin in plants." Plant physiology 123.4 (2000): 1483-1494.
Ghetie, Maria-Ana, et al. "Homodimerization of tumor-reactive monoclonal antibodies markedly increases their ability to induce growth arrest or apoptosis of tumor cells." Proceedings of the National Academy of Sciences 94.14 (1997): 7509-7514.
Goel, Apollina, et al. "Genetically engineered tetravalent single-chain Fv of the pancarcinoma monoclonal antibody CC49: improved biodistribution and potential for therapeutic application." Cancer Research 60.24 (2000): 6964-6971.
Köhler, Georges, and Cesar Milstein. "Continuous cultures of fused cells secreting antibody of predefined specificity." nature 256.5517 (1975): 495.

* cited by examiner

*Primary Examiner* — Gary B Nickol
*Assistant Examiner* — Lakia J Jackson-Tongue
(74) *Attorney, Agent, or Firm* — Frost Brown Todd LLC

(57) ABSTRACT

An isolated antibody, consisting of an anti-glutathionylated eNOS antibody, wherein the anti-glutathionylated eNOS antibody has been generated against an immunogen consisting of a peptide that includes glutathione; a first linker; an eNOS peptide; a second linker; and a T-cell epitope; and wherein the anti-glutathionylated eNOS antibody is adapted to recognize redox modulated eNOS proteins.

13 Claims, 7 Drawing Sheets

Specification includes a Sequence Listing.

```
659  HPCAFARAVDTRLEELGERRLLQLQ[RPELCRQEE]FRERAQAAFQAACETFCVGEDARA  718  P29474  NOS3_HUMAN
658  HPCAFARAVDTRLEELGERRLLQLQ[RPELCRQEE]FRERAQAAFQAACETFCVGEDARA  717  Q62600  NOS3_RAT
658  HPCAFARAVDTRLEELGERRLLQLQ[RPELCRQEE]FRERAQAAFQAACETFCVGEDARA  717  P70313  NOS3_MOUSE
```

FIG. 1

1) Immunogen

Glutathione    eNOS                        MVF
                                               T cell epitope
    GCEGPSLSSGDELCGQEEGPSLKLLSLIKGVIVHRLEGVE
        L1                    L2
        B cell epitope

FIG. 2A

2) Gp
(Glu-eNOSpep, + C)

GCE (Glutathione)
  |
GDELCGQEE (eNOS 9 mer)

FIG. 2B

3) NGp
(NonGlu-eNOSpep, - C)

GDELCGQEE

FIG. 2C

4) GSH
(Glutathione)

GCE

FIG. 2D

Glu-eNOSpep (Gp, + C)

| 1A9 | 1C6 | 1E7 | 1E9 | 1E10 | 1G12 | 2C10 | 2E12 | 2F8 | 3C9 | 3F1 | 4B7 |
|---|---|---|---|---|---|---|---|---|---|---|---|
| 0.0304 | -0.0273 | -0.0307 | 0.1879 | -0.0306 | -0.0318 | -0.0309 | 0.0143 | 0.0010 | 0.0330 | 0.1830 | 0.0737 |

| 4C10 | 4E6 | 4E12 | 4G3 | 5A2 | 5F8 | 6A4 | CarSer | NaiSer | Media |
|---|---|---|---|---|---|---|---|---|---|
| 0.0860 | 0.0038 | -0.0091 | 0.1198 | 0.0738 | 0.1028 | 0.1334 | 1.0483 | -0.0038 | 0 |

FIG. 3A

NonGlu-eNOSpep (NGp, - C)

| 1A9 | 1C6 | 1E7 | 1E9 | 1E10 | 1G12 | 2C10 | 2E12 | 2F8 | 3C9 | 3F1 | 4B7 |
|---|---|---|---|---|---|---|---|---|---|---|---|
| 0.0617 | -0.0314 | -0.0435 | 0.5632 | -0.0255 | -0.0481 | -0.0344 | 0.023 | 0.0023 | 0.056 | 0.1913 | 0.0899 |

| 4C10 | 4E6 | 4E12 | 4G3 | 5A2 | 5F8 | 6A4 | CarSer | NaiSer | Media |
|---|---|---|---|---|---|---|---|---|---|
| 0.4286 | 0.0353 | 0.0016 | 0.2858 | 0.1449 | 0.2726 | 0.1624 | 0.1172 | -0.0047 | -3E-05 |

FIG. 3B

Glutathione (GSH)

| 1A9 | 1C6 | 1E7 | 1E9 | 1E10 | 1G12 | 2C10 | 2E12 | 2F8 | 3C9 | 3F1 | 4B7 |
|---|---|---|---|---|---|---|---|---|---|---|---|
| 0.0762 | -0.0206 | -0.0039 | 0.4256 | -0.0258 | -0.0045 | -0.0161 | 0.052 | 0.0497 | 0.0809 | 0.1841 | 0.1297 |

| 4C10 | 4E6 | 4E12 | 4G3 | 5A2 | 5F8 | 6A4 | CarSer | NaiSer | Media |
|---|---|---|---|---|---|---|---|---|---|
| 0.4376 | 0.1482 | 0.0737 | 0.4494 | 0.113 | 1.0786 | 0.1676 | 0.6209 | 0 | 0 |

FIG. 3C

Immunogen

| 1A9 | 1C6 | 1E7 | 1E9 | 1E10 | 1G12 | 2C10 | 2E12 | 2F8 | 3C9 | 3F1 | 4B7 |
|---|---|---|---|---|---|---|---|---|---|---|---|
| 3.000 | 1.794 | 0.984 | 3.000 | 1.464 | 0.952 | 0.923 | 3.000 | 3.000 | 0.641 | 2.853 | 3.000 |

| 4C10 | 4E6 | 4E12 | 4G3 | 5A2 | 5F8 | 6A4 | CarSer | NaiSer | Media |
|---|---|---|---|---|---|---|---|---|---|
| 3.000 | 3.000 | 1.011 | 1.106 | 2.895 | 3.000 | 2.722 | 3.000 | 0 | 0.225 |

FIG. 3D

−DA −DTT

+DA −DTT

+DA +DTT

+DA −DTT +Gp

ANTIBODIES FOR DETECTING REDOX MODULATED PROTEINS

CROSS-REFERENCE TO RELATED APPLICATIONS

This patent application is a continuation-in-part of U.S. patent application Ser. No. 14/753,759 filed on Jun. 29, 2015 and entitled "Compositions and Methods for Redox Modulated Proteins", which was a continuation of U.S. patent application Ser. No. 13/051,425 (now U.S. Pat. No. 9,067,982) filed on Mar. 18, 2011 and entitled "Compositions and Methods for Redox Modulated Proteins", which claimed the benefit of U.S. Provisional Application No. 61/340,458, filed on Mar. 18, 2010, the disclosures of which are hereby incorporated by reference herein in its entirety and made part of the present U.S. utility patent application for all purposes.

REFERENCE TO A SEQUENCE LISTING

A sequence listing in computer readable form (CRF) is on file. The sequence listing is in an ASCII text (.txt) file entitled SEQ ID NO 1-7 created on Sep. 7, 2018 and is 4 KB in size. The sequence listing is incorporated by reference as if fully recited herein.

BACKGROUND OF THE INVENTION

The described invention relates in general to systems, methods, and compositions for detecting redox modulated proteins, and more specifically to antibodies for detecting redox modulated proteins including glutathionylated proteins.

Recent scientific research indicates that increased levels of redox modulated proteins in mammals are critical indicators of cellular stress and disease states. Redox is a change in oxidation, and its occurrence signals a change in cellular function. Detecting redox modulated proteins with specificity and measuring the respective levels thereof is critical for understanding the mechanisms of redox homeostasis that are occurring in certain disease processes. The detection of these proteins facilitates understanding of the redox modification of a specific protein that undergoes redox modifications occurring early in disease processes, thereby allowing earlier intervention in the disease process and the prevention of further cellular damage. However, because the significance of these proteins is a relatively new discovery, little advancement has been made with regard to detecting redox modulated proteins and few methods and compositions exist for detecting and measuring redox modulated proteins with any degree of specificity. Currently available tools such as analytical and proteomic approaches are not sensitive or cost effective and are not compatible with direct visualization techniques. Accordingly, there is a need for better systems, devices, methods, and compositions for detecting redox modulated proteins and further understanding the role thereof in numerous diseases including, for example, Alzheimer's disease, atherosclerosis, hypertension, cancer, and diabetes.

SUMMARY OF THE INVENTION

The following provides a summary of certain exemplary embodiments of the present invention. This summary is not an extensive overview and is not intended to identify key or critical aspects or elements of the present invention or to delineate its scope. However, it is to be understood that the use of indefinite articles in the language used to describe and claim the present invention is not intended in any way to limit the described system. Rather the use of "a" or "an" should be interpreted to mean "at least one" or "one or more".

In accordance with one aspect of the present invention, a first isolated antibody is provided. This isolated antibody includes an anti-glutathionylated endothelial nitric oxide synthase (eNOS) antibody, wherein the anti-glutathionylated eNOS antibody has been generated against an immunogen consisting of a peptide that includes glutathione; a first linker; an eNOS peptide; a second linker; and a T-cell epitope; and wherein the anti-glutathionylated eNOS antibody is adapted to recognize redox modulated eNOS proteins. In some embodiments, the isolated antibody is polyclonal and in other embodiments, the isolated antibody is monoclonal.

In accordance with another aspect of the present invention, a second isolated antibody is provided. This second isolated antibody includes an anti-glutathionylated eNOS antibody, wherein the anti-glutathionylated eNOS antibody has been generated against an immunogen consisting of a peptide that includes glutathione; a first linker, an eNOS peptide; a second linker; a T-cell epitope, and that has an amino acid sequence consisting of SEQ ID NO. 4; and wherein the anti-glutathionylated eNOS antibody is adapted to recognize redox modulated eNOS proteins, wherein the redox modulated protein is a glutathionylated protein. In some embodiments, the isolated antibody is polyclonal and in other embodiments, the isolated antibody is monoclonal.

In yet another aspect of this invention, a method for generating an antibody that recognizes redox modulated proteins. This antibody is an anti-glutathionylated eNOS antibody and the method for generating the antibody includes providing an immunogen consisting of a peptide that includes glutathione; a first linker; an eNOS peptide; a second linker; and a T-cell epitope; immunizing a selected mammal with the immunogen; isolating the blood serum from the immunized mammal containing antibodies; isolating antibody-producing cells taken from the spleen or lymph node of the immunized mammal; fusing the isolated antibody-producing cells with myeloma cells resulting in a hybridoma; cloning the hybridoma and recovering monoclonal antibodies; and purifying the monoclonal antibodies using a glutathionylated peptide.

Additional features and aspects of the present invention will become apparent to those of ordinary skill in the art upon reading and understanding the following detailed description of the exemplary embodiments. As will be appreciated by the skilled artisan, further embodiments of the invention are possible without departing from the scope and spirit of the invention. Accordingly, the drawings and associated descriptions are to be regarded as illustrative and not restrictive in nature.

BRIEF DESCRIPTION OF THE DRAWINGS

The accompanying drawings, which are incorporated into and form a part of the specification, schematically illustrate one or more exemplary embodiments of the invention and, together with the general description given above and detailed description given below, serve to explain the principles of the invention, and wherein:

FIG. 1 is a comparison of eNOS amino acid sequences from selected species including human nitric oxide synthase (SEQ ID NO: 1), rat nitric oxide synthase (SEQ ID NO: 2), and mouse nitric oxide synthase (SEQ ID NO: 3) showing sequence similarity across different species and monoclonal antibody generated to the glutathionylated cysteine and amino acids in the boxed region;

FIG. 2A is the amino acid sequence for an immunogen peptide (SEQ ID NO: 4) in accordance with an exemplary embodiment of the present invention, wherein the immunogen peptide includes glutathione; Linker 1 (L1); eNOS 685-693; Linker 2 (L2); and measles virus fusion protein (MVF)/T-cell epitope;

FIG. 2B is the amino acid sequence for a glutathionylated eNOS peptide (Gp) (SEQ ID NO: 5);

FIG. 2C is the amino acid sequence for a non-glutathionylated eNOS peptide (NGp) (SEQ ID NO: 6);

FIG. 2D is the amino acid sequence for glutathione (GSH) (SEQ ID NO: 7);

FIGS. 3A-D are tables showing the ELISA immunoreactivity of antibodies secreted by hybridoma clones (1A9, 1C6, 1E7, 1E9, 1E10, 1G12, 2C10, 2E12, 2F8, 3C9, 3F1, 4B7, 4C10, 4E6, 4E12, 4G3, 5A2, 5F8, 6A4), Cardiac Serum (CarSer), pre-immune Naïve Serum (NaiSer), hybridoma culture media (Media) to positive control peptide (glutathionylated-eNOS peptide (FIG. 3A); negative control peptide (non-glutathionylated eNOS peptide)(FIG. 3B); glutathione (GSH)(FIG. 3C); and immunogen peptide (the immunogen peptide of FIG. 2A)(FIG. 3D);

FIG. 5A-D are a series of photomicrographs that include immuno-staining and confocal images of bovine aortic endothelial cells (BAEC), wherein FIG. 5A shows control cells not treated with diamide and DTT; wherein FIG. 5B shows cells treated with diamide (25 uM) and without DTT treatment; wherein FIG. 5C shows cells treated with diamide (25 uM) and DTT (100 uM); wherein FIG. 5D shows cells treated with diamide (25 uM), not treated with DTT and pre-incubated with glutathionylated eNOS peptide (5 ug); and wherein antibody 5F8 pre-treated with 5 ug eNOS peptide (Glu-eNOSpep shown in FIG. 2B) did not bind with cellular (BAEC) GeNOS protein, thereby confirming specificity to GeNOS Antibody;

FIGS. 6A-C are a series of photomicrographs that include immunocytochemical localization and confocal microscopy of glutathionylated eNOS in human aortic endothelial cells (HAEC) treated with (40 uM) menadione or menadione (40 uM) and DTT (100 uM), wherein FIG. 6B shows the characteristic perinuclear/plasma membrane staining of GeNOS in HAECs treated with Menadione (40 uM) when compared to untreated cells (FIG. 6A) or menadione (40 uM) and DTT (100 uM) treated cells (FIG. 6C)

DETAILED DESCRIPTION OF THE INVENTION

Figures 4A, 4C, 4E, 4G:
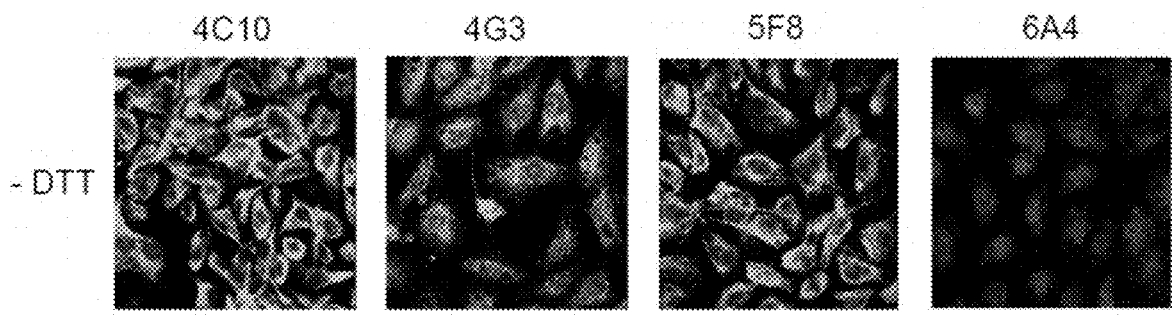
FIGS. 4A-H are a series of photomicrographs that include immuno-staining and confocal images of purified 4C10, 4G3, 5F8, 6A4 clone antibodies and bovine aortic endothelial cells (BAEC) treated with menadione (25 uM), and without DTT (−DTT) or with DTT (+DTT, 100 uM), wherein a blue and green staining pattern indicates nuclei (stained with DAPI) and glutathionylated eNOS antibodies, wherein only the photomicrographs showing the staining of the 5F8 antibody demonstrate binding with GeNOS and removal with DTT treatment, and wherein other antibodies (4C10, 4G3) were either bound with cells and not removed by DTT treatment, or demonstrated only weak binding (6A4)
Figures 4B, 4D, 4F, 4H:
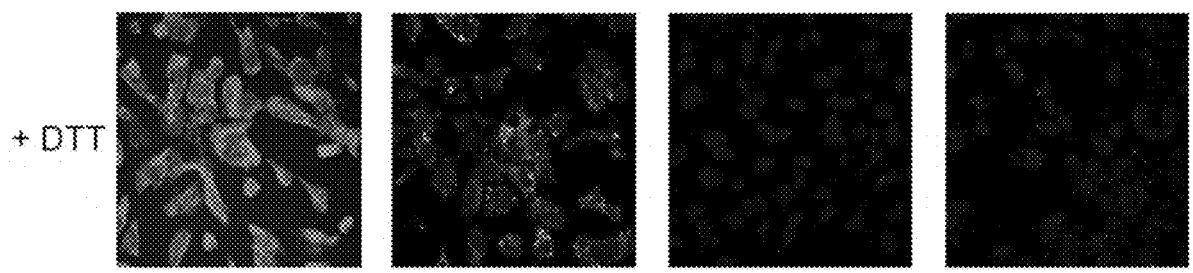

Exemplary embodiments of the present invention are now described with reference to the Figures. Reference numerals are used throughout the detailed description to refer to the various elements and structures. Although the following detailed description contains many specifics for the purposes of illustration, a person of ordinary skill in the art will appreciate that many variations and alterations to the following details are within the scope of the invention. Accordingly, the following embodiments of the invention are set forth without any loss of generality to, and without imposing limitations upon, the claimed invention.

The present invention relates to systems, methods, and compositions for detecting redox modulated proteins. The present invention also relates to methods and compositions for preventing, treating or ameliorating or detecting disease and/or symptoms related to redox modulated proteins including glutathionylated proteins (GSSP), and for studying the mechanisms involved in animal/human diseases. These methods include administering to an animal, preferably a human, an effective amount of one or more antibodies or fragments or variants thereof, or related molecules, that specifically bind to a redox modulated protein or a fragment or variant thereof. In specific embodiments, the present invention relates to methods and compositions for preventing, treating or ameliorating a disease or disorder associated with redox modulated proteins including glutathionylated proteins, comprising administering to an animal, preferably a human, an effective amount of one or more antibodies or fragments or variants thereof, or related molecules, that specifically bind a redox modulated protein or a fragment or variant thereof.

Various embodiments of this invention include systems, methods, and compositions for identifying S-glutathionylated proteins (GSSP) and exploring the cellular significance of these modifications with respect to such proteins, diagnosing diseases related to redox modulated proteins, and methods and compositions for treating those diseases. Protein S-Glutathionylation and Protein S-Nitrosylation are examples of redox modulated proteins. Conjugation of glutathione to protein cysteinyl residues, called protein S-glutathionylation, is a critical mechanism in regulating the functions of enzymes, signaling molecules, transcription factors, heat shock proteins, ion channels, mitochondrial proteins, and cytoskeletal proteins. During oxidative stress, GSSP level increases and are controlled by glutaredoxins under physiological conditions. This modification helps in protecting the protein from (i) irreversible oxidation; and (ii) modulation of protein function, thus preserving the vital functions of the cells. Impaired deglutathionylation of the functionally critical cysteine residues leads to protein inactiveness and thus impaired protein function. Due to the imbalance in glutathionylation or deglutathionylation process the formation of GSSP is increased irreversibly in stress/disease conditions, which leads to protein adduct formation. S-glutathionylated proteins have been identified in the following human diseases; Actin—Ischemia/Cardiovascular disease and Friedreich's ataxia, Tau—Alzheimer's disease, Hemoglobin—Type 2 diabetes, CTFR—Cystic fibrosis, γ-S-crystallin—Cataract disease, Spectrin—Sickle cell anemia.

The present invention also includes antibodies that recognize redox modulated proteins such as glutathionylated eNOS. Endothelial NOS (eNOS—also known as nitric oxide synthase 3 (NOS3)) is an enzyme that synthesizes nitric oxide (NO), a small gaseous and lipophilic molecule that participates in several biological processes. eNOS is primarily responsible for the generation of NO in the vascular endothelium a monolayer of flat cells lining the interior surface of blood vessels, at the interface between circulating blood in the lumen and the remainder of the vessel wall. NO produced by eNOS in the vascular endothelium plays crucial roles in regulating vascular tone, cellular proliferation, leukocyte adhesion, and platelet aggregation. Therefore, a functional eNOS is essential for a healthy cardiovascular system. eNOS has a protective function in the cardiovascular system, which is attributed to NO production. Regulation of the vascular tone is one of the best-known roles of NO in the cardiovascular system. Certain embodiments relate to a reagent for the immunoassay of glutathionylated eNOS. Disclosed embodiments also relate to diagnosis of and therapies for the treatment of diseases related to impaired deglutathionylation of peptides. Another embodiment includes the use of the antibodies disclosed herein as a diagnostic tool for monitoring the presence of redox modulated proteins including glutathionylated proteins, for example GSS-eNOS.

The present invention also provides anti-GSSP antibodies that are coupled to a detectable label, such as an enzyme, a fluorescent label, a luminescent label, or a bioluminescent label. The present invention also provides a tool for the detection of redox modulated protein that could serve in finding a therapeutic agent. The present invention also provides redox modulated protein antibodies that are coupled, directly or indirectly, to a fluorescent tag/radioactive material. The present invention also provides a method for the production of an antibody (including a molecule comprising, or alternatively consisting of, an antibody fragment or variant thereof) of the invention. The present invention further provides a method of expressing an antibody (including a molecule comprising, or alternatively consisting of, an antibody fragment or variant thereof) of the invention from a nucleic acid molecule. These and other aspects of the invention are described in further detail below.

Cluster analysis of proteins susceptible to S-glutathionylation is summarized below;

| Function | Protein |
|---|---|
| Energy metabolism | ATPase, NADPH, GAPDH, Pyruvate kinase, Pyruvate dehydrogenase, Phosphoglycerate kinase, Triose phosphate isomerase, aldolase, α-ketoglutarate dehydrogenase, Mitochondrial isocitrate dehydrogenase, Complex 1, NADH ubiquinone reductase, Carbonic anhydrase III, Catechol-O-methyltransferase |
| Cytoskeleton | Actin, Spectrin, Tubulin, Vimentin |
| Signaling | Creatinine kinase, PKC, PKG, cAMP dependent PKA, MEKK1 (JNK), Protein tyrosine phosphatase1B, PTEN, Pyrophosphatase 2A, NFκB, subunits 65 and 50, c-able, p53, Caspase 3, GTPase, p21 ras, Keap1, Nrf2 |
| Calcium homeostasis | SERCA, RyR I & II, S100A1, S100B, CTFR |
| Protein folding | HSP 65, 70, PDI, Ubiquitin conjugating enzyme, 20S Proteosome |
| Redox | Glutathione S-transferase, Nitric Oxide Synthases, Thioredoxin 1, Peroxiredoxin |

List of S-nitrosylated proteins in disease conditions is given below.

| Protein | Diseases |
|---|---|
| Dyanin related protein-1, Parkin, Peroxiredoxin 2, Protein disulfide isomerase, X-linked inhibitor of apoptosis, Glyceraldehyde 3-phosphate dehydrogenase | Alzheimer's disease/Parkinson's disease |
| HIF-1 alpha | Angiogenesis/pulmonary arterial hypertension |
| Ras | Adaptive immunity/tumor maintenance |
| Arginase, glutathione | Asthma/Endothelial dysfunction |
| Glutathione | Cystic Fibrosis |
| Cardiac Ryanodine receptor, Nitric Oxide Synthases | Heart failure |
| Insulin receptor beta, Insulin receptor substrate 1, Protein kinase b | Diabetes (Type II) |
| Hemoglobin | Type I Diabetes/Pulmonary arterial hypertension/Sickle cell anemia |
| Serum Albumin | Preeclampsia |
| Ryanodine receptor 1 | Muscle fatigue/muscular dystrophy (duschenne)/Sudden cardiac death |
| Matrix metalloproteinase 9 | Stroke |

A list of antibody sets for heart and cardiovascular related research follows:
I. Hypertrophy Markers:
  1) ANF—Arterial natriuretic factor/peptide
  2) BNF—brain natriuretic factor/peptide
  3) alpha-MHC/myosin-heavy chain
  4) B-MHC
  5) Phospholamban (PLN)
  6) SERCA2A
  7) PGC1-alpha
II. Cardiac Defense:
  1) Sod-1
  2) Catalase
  3) Gpx-1
  4) G6PDH
  5) GSR
  6) Thoredoxin-1
  7) Gamma-GCS
III. Cardiac Stress/Chaperones:
  1) Hsp 22/alpha-B-Crystallin
  2) Hsp 25/Hsp 27 (in rat and human)
  3) Hsp 47 (cardiac remodeling)
  4) Hsp 70 (constitutive)
  5) Hsp 70i (inducible)
  6) Hsp 90 (gene regulation)
  7) Hsp20/cvHSP (cardiovascular HSP)
IV. Cardiac Hypertrophy/Signaling:
  1) Akt/p-Akt
  2) GSK3-alpha
  3) GSK3-B
  4) ERK 1/2
  5) p-ERK 1/2
  6) Map38/41 and phospho
V. Cardiac Gene-Regulation:
  1) Hsp90
  2) Hdac-1
  3) Hdac-3
  4) Hdac-4
  5) Hdac-5
  6) Hdac-6
VI. Cardiac Oxidative Stress Markers:
  1) DNPH (protein oxidation)
  2) Nitrotyrosine 3) Glutathione (s-glutathionylation)
4) Ubiquitin (ubiquitination)
5) Proteasome-21 (proteosome dysfunction)

VII. Cardiac Mitochondrial Stress/Biogenesis:
1) PGC1-alpha
2) Hsp-60
3) Sod-2
4) Thioredoxin-2
5) Aconitase VIII. Cardiac Mito Dysfunction:
1) Complex-1—sub units (set of 6)
2) Complex-3 sub units—(set of 6)
3) VDAC (voltage dependent anion channel)—MPTP opening
4) ANT (adenine nucleotide translocase)—MPTP
5) Cyclophilin-D—MPTP IX. Hypertension/Cardiac Hypertrophy:
1) TNF-alpha
2) TNF-alpha Receptro 1
3) TNF-alpha receptor 2
4) Nox-2/Gp91 phox
5) Nox-4/Gp21 phox
6) IL-6
7) IL-10

X. Cardiac NO Related:
1) eNOS
2) p-eNOS
3) Endothelin-1
4) Endothelin-receptor—A/ET-ra
5) Endothelin-receptor—B/ET-rb XI. Cardiac apoptosis:
1) Bcl-2
2) Bax
3) Caspase-3
4) Cleaved caspase-3
5) Caspase-9
6) AIF (apoptosis inducing factor)

FIG. 1 is a comparison of eNOS amino acid sequences from selected species including human nitric oxide synthase (SEQ ID NO: 1), rat nitric oxide synthase (SEQ ID NO: 2), and mouse nitric oxide synthase (SEQ ID NO: 3) showing sequence similarity across different species and monoclonal antibody generated to the glutathionylated cysteine and amino acids in the boxed region.

Unless otherwise defined, all technical and scientific terms used herein have the same meaning as commonly understood by one of ordinary skill in the art to which these embodiments pertain. Although methods and materials similar or equivalent to those described herein can be used in the practice or testing of various embodiments, suitable methods and materials are described below. All publications, patent applications, patents, and other references mentioned herein are incorporated by reference in their entirety for all purposes. In case of conflict, the present specification, including definitions, will control. In addition, the materials, methods, and examples are illustrative only and not intended to be limiting.

The section headings used herein are for organizational purposes only and are not to be construed as limiting the described subject matter in any way. It will be appreciated that there is an implied "about" prior to metrics such as temperatures, concentrations, and times discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the invention. The articles "a" and "an" are used herein to refer to one or to more than one (i.e., to at least one) of the grammatical object of the article. By way of example, "an element" means one element or more than one element.

As used herein, the term "subject" is intended to include humans, non-human animals, and plants. The term "non-human animals" includes all vertebrates, e.g., mammals and non-mammals, such as non-human primates, pigs, chickens and other birds, mice, dogs, cats, cows, and horses.

The antibody according to the present invention includes a polyclonal antibody, a monoclonal antibody, a chimeric antibody, a single chain antibody (scFv), a humanized antibody, and a multi-specific antibody. Also, the fragment of the antibody according to the present invention includes an antibody fragment such as Fab, Fab', F(ab')$_2$, Fc, and Fv.

An "isolated antibody" is an antibody removed from its native environment. Thus, an antibody produced by, purified from and/or contained within a hybridoma and/or a recombinant host cell is considered isolated for purposes of the present invention.

In embodiments that include preparation of a polyclonal antibody, blood can be taken from a mammal sensitized with an antigen and blood serum can be isolated with known procedures from the blood to yield blood serum containing the polyclonal antibody. As needed, a fraction containing the polyclonal antibody can further be isolated from this blood serum.

For a monoclonal antibody, antibody-producing cells are taken from spleen or lymph-node of a mammal sensitized with the above-mentioned antigen, and then undergo cell fusion with myeloma cell. The resultant hybridoma is subjected to cloning and the antibody was recovered from the culture thereof to yield the monoclonal antibody.

A fragment of the abnormal protein can be used as an immunogen. Alternatively, the synthesized one based on the amino acid sequence of the abnormal protein can be used. The antigen can be used as a complex with a carrier protein. A variety of condensing agents can be used for preparation of the complex between the antigen and the carrier protein, which condensing agents include glutaraldehyde, carbodiimide, and maleimide active ester. The carrier protein may be a usually used one such as bovine serum albumin, thyroglobulin, and hemocyanin. A procedure for coupling at a rate (volume) of 1 time to 5 times is usually employed.

Examples of the animal immunized include mice, rats, rabbits, guinea pigs, hamsters. An example of a method of inoculation is subcutaneous, intramuscular or intraperitoneal administration.

The antibody-producing cells obtained from the spleen or lymph-node of the animal immunized undergo cell fusion with myeloma cells and are isolated as hybridomas. Because myeloma cells, and cells derived from mouse, rat, *Homo sapiens*, etc. are used, it is preferred that antibody-producing cell be derived from the same species. However, there are cases where the cell fusion can be carried out between different species.

Procedures for cell fusion may be carried out using known methods (see, for example, *Nature*, 256, 495, 1975). Examples of fusion accelerators include polyethylene glycols and the Sendai virus. Cell fusion is typically conducted by using about 20-50% of concentration of polyethylene glycols (average molecular weight 1000 to 4000); at a temperature of 20 to 40° C. (preferably 30 to 37° C.); at a ratio in number of cells between antibody production cells and myeloma of about 1:1 to 10:1; for about 1 to 10 minutes.

Various immunochemical methods can be employed for screening the antibody-producing hybridoma. Examples thereof include ELISA method using a microtiter plate coated with the abnormal protein, EIA method using a microtiter plate coated with an anti-immunoglobulin antibody, immune blot method using a nitrocellulose blotting membrane after electrophoresis of samples containing the abnormal protein.

Using such wells, cloning by, for example, a limiting dilution method can be further carried out to obtain a clone. Selection of the hybridoma is usually carried out in culture medium for mammalian cells (such as, for example, RPM11640) and supplemented with HAT (hypoxanthine, aminopterin, and thymidine). A clone obtained in such a way is intraperitoneally transplanted into a SCID mouse previously administrated with pristine. Ten to fourteen days later, ascites containing the monoclonal antibody at a high concentration is obtained and can be used as a raw material for antibody purification. Also, the clone may be cultured, and any obtained culture may be used as a raw material for antibody purification.

Any purification method may be used for purifying the monoclonal antibody provided it is a known method for purifying an immunoglobulin. Purification can be readily accomplished by, for example, an ammonium sulfate fractionation method, a PEG fractionation method, an ethanol fractionation method, use of an anion exchanger, as well as processes and techniques such as affinity chromatography using the abnormal protein.

In embodiments that include preparation of a polyclonal antibody, purification of the polyclonal antibody from serum can be carried out in the same manner as previously described.

Also provided are various kits for performing the methods provided herein. Additionally, any such kit may include instructional materials for performing the various methods presented herein. These instructions may be printed and/or may be supplied, without limitation, as an electronic-readable medium, such as a floppy disc, a CD-ROM, a DVD, a Zip disc, a video cassette, an audiotape, and/or a flash memory device. Alternatively, instructions may be published on an internet web site or may be distributed to the user as an electronic mail. When a kit is supplied, the different components thereof can be packaged in separate containers. Such packaging of the components separately can permit long-term storage without losing the active components' functions.

Unless otherwise defined in the specification, specific binding of an antibody to a redox modulated protein, such as glutathionylated eNOS, means that an antibody binds the redox modulated protein but does not significantly bind to (i.e., cross react with) proteins other than the redox modulated protein, such as other proteins in the same family of proteins). An antibody that binds the redox modulated protein and does not cross-react with other proteins is not necessarily an antibody that does not bind said other proteins in all conditions; rather, the redox modulated protein-specific antibody of the invention preferentially binds the redox modulated protein compared to its ability to bind other proteins such that it will be suitable for use in at least one type of assay or treatment, i.e., give low background levels or result in no unreasonable adverse effects in treatment. It is well known that the portion of a protein bound by an antibody is known as the epitope. An epitope may either be linear (i.e., comprised of sequential amino acids residues in a protein sequences) or conformational (i.e., comprised of one or more amino acid residues that are not contiguous in the primary structure of the protein but that are brought together by the secondary, tertiary or quaternary structure of a protein). Additionally, redox modulated protein-specific antibodies of the invention may bind modified forms of the redox modulated protein, for example, fusion proteins. In such a case when antibodies of the invention bind fusion proteins, the antibody must make binding contact with the redox modulated protein moiety of the fusion protein in order for the binding to be specific. Antibodies that specifically bind to the redox modulated protein can be identified, for example, by immunoassays or other techniques known to those of skill in the art.

Antibodies of the invention may also include multimeric forms of antibodies. For example, antibodies of the invention may take the form of antibody dimers, trimers, or higher-order multimers of monomeric immunoglobulin molecules. Dimers of whole immunoglobulin molecules or of $F(ab')_2$ fragments are tetravalent, whereas dimers of Fab fragments or scFv molecules are bivalent. Individual monomers within an antibody multimer may be identical or different, i.e., they may be heteromeric or homomeric antibody multimers. For example, individual antibodies within a multimer may have the same or different binding specificities. Multimerization of antibodies may be accomplished through natural aggregation of antibodies or through chemical or recombinant linking techniques known in the art. For example, some percentage of purified antibody preparations (e.g., purified IgG1 molecules) spontaneously form protein aggregates containing antibody homodimers, and other higher-order antibody multimers. Alternatively, antibody homodimers may be formed through chemical linkage techniques known in the art. For example, heterobifunctional crosslinking agents including, but not limited to, SMCC [succinimidyl 4-(maleimidomethyl) cyclohexane-1-carboxylate] and SATA [N-succinimidyl S-acethylthio-acetate] (available, for example, from Pierce Biotechnology, Inc. (Rockford, Ill.)) can be used to form antibody multimers. An exemplary protocol for the formation of antibody homodimers is given in Ghetie et al., Proceedings of the National Academy of Sciences USA (1997) 94:7509-7514, which is hereby incorporated by reference in its entirety for all purposes. Antibody homodimers can be converted to Fab'2 homodimers through digestion with pepsin. Alternatively, antibodies can be made to multimerize through recombinant DNA techniques. IgM and IgA naturally form antibody multimers through the interaction with the J chain polypeptide. Non-IgA or non-IgM molecules, such as IgG molecules, can be engineered to contain the J chain interaction domain of IgA or IgM, thereby conferring the ability to form higher order multimers on the non-IgA or non-IgM molecules. (see, for example, Chintalacharuvu et al., (2001) Clinical Immunology 101:21-31 and Frigerio et al., (2000) Plant Physiology 123:1483-94, both of which are hereby incorporated by reference in their entireties.). ScFv dimers can also be formed through recombinant techniques known in the art; an example of the construction of scFv dimers is given in Goel et al., (2000) Cancer Research 60:6964-6971, which is hereby incorporated by reference in its entirety. Antibody multimers may be purified using any suitable method known in the art, including, but not limited to, size exclusion chromatography.

The term "variant" as used herein refers to a polypeptide that possesses a similar or identical amino acid sequence as a redox modulated protein polypeptide, a fragment of a redox modulated protein polypeptide, a redox modulated protein antibody or antibody fragment thereof. A variant having a similar amino acid sequence refers to a polypeptide that satisfies at least one of the following: (a) a polypeptide comprising, or alternatively consisting of, an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of redox modulated protein polypeptide such as GSS-eNOS, a fragment of a redox modulated protein polypeptide, a GSS-eNOS antibody or antibody fragment thereof.

The term "derivative" as used herein, refers to a variant polypeptide of the invention that comprises, or alternatively consists of, an amino acid sequence of a redox modulated protein polypeptide, a fragment of a redox modulated protein polypeptide, or an antibody of the invention that specifically binds to a redox modulated protein polypeptide, which has been altered by the introduction of amino acid residue substitutions, deletions or additions. The term "derivative" as used herein also refers to a redox modulated protein polypeptide, a fragment of a redox modulated protein polypeptide, an antibody that specifically binds to a redox modulated protein polypeptide which has been modified, e.g., by the covalent attachment of any type of molecule to the polypeptide. For example, but not by way of limitation, a redox modulated protein polypeptide, a fragment of a redox modulated protein polypeptide, or a redox modulated protein antibody, may be modified, e.g., by glycosylation, acetylation, pegylation, phosphorylation, amidation, derivatization by known protecting/blocking groups, proteolytic cleavage, linkage to a cellular ligand or other protein, etc. A derivative of a redox modulated protein polypeptide, a fragment of a redox modulated protein polypeptide, or a redox modulated protein antibody, may be modified by chemical modifications using techniques known to those of skill in the art, including, but not limited to, specific chemical cleavage, acetylation, formylation, metabolic synthesis of tunicamycin, etc. Further, a derivative of a redox modulated protein polypeptide, a fragment of a redox modulated protein polypeptide, or a redox modulated protein antibody, may contain one or more non-classical amino acids. A polypeptide derivative possesses a similar or identical function as a redox modulated protein polypeptide, a fragment of a redox modulated protein polypeptide, or a redox modulated protein antibody, described herein.

The term "fragment" as used herein refers to a polypeptide comprising an amino acid sequence of at least 5 amino acid residues, at least 10 amino acid residues, at least 15 amino acid residues, at least 20 amino acid residues, at least 25 amino acid residues, at least 30 amino acid residues, at least 35 amino acid residues, at least 40 amino acid residues, at least 45 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues, of the amino acid sequence of a redox modulated protein, or a redox modulated protein antibody (including molecules such as scFv's, that comprise, or alternatively consist of, antibody fragments or variants thereof) that specifically binds to a redox modulated protein such as GSS-eNOS.

Antibodies of the present invention are preferably provided in an isolated form, and preferably are substantially purified. An "isolated" is an antibody removed from its native environment. Thus, for example, an antibody produced and/or contained, within a recombinant host cell is considered isolated for purposes of the present invention.

In certain embodiments, the antibodies of the present invention specifically bind a redox modulated protein polypeptide. An antibody that specifically binds redox modulated protein may, in some embodiments, bind fragments, variants (including species orthologs of redox modulated proteins), multimers or modified forms of redox modulated proteins. For example, an antibody specific for GSS-eNOS may bind the GSS-eNOS moiety of a fusion protein comprising all or a portion of the redox modulated protein.

Redox modulated proteins may be found as monomers or multimers (i.e., dimers, trimers, tetramers, and higher multimers). Accordingly, the present invention relates to antibodies that bind redox modulated proteins found as monomers or as part of multimers. In specific embodiments, antibodies of the invention bind redox modulated protein monomers, dimers, trimers or heptamers. In additional embodiments, antibodies of the invention bind at least dimers, at least trimers, or at least tetramers containing one or more redox modulated protein polypeptides.

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. As such, disclosed embodiments relate to antibodies resulting from the introduction of peptides or polypeptides bearing an antigenic epitope used to mimic the native protein.

A variety of host-expression vector systems may be utilized to express the antibody molecules of this application. Such host-expression systems represent vehicles by which the coding sequences of interest may be produced and subsequently purified, but also represent cells which may, when transformed or transfected with the appropriate nucleotide coding sequences, express an antibody molecule of the invention in situ.

Once an antibody molecule of the present invention (including molecules comprising, or alternatively consisting of, antibody fragments or variants thereof) has been chemically synthesized or recombinantly expressed, it may be purified by any method known in the art for purification of an immunoglobulin molecule, or more generally, a protein molecule, such as, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention may be fused to heterologous polypeptide sequences described herein or otherwise known in the art, to facilitate purification.

Antibodies of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the antibodies of the present invention may be glycosylated or may be non-glycosylated. In addition, antibodies of the invention may also include an initial modified methionine residue, in some cases as a result of host-mediated processes.

Antibodies of the invention can be chemically synthesized using techniques known in the art. For example, a peptide corresponding to a fragment of an antibody of the invention can be synthesized by use of a peptide synthesizer. Furthermore, if desired, nonclassical amino acids or chemical amino acid analogs can be introduced as a substitution or addition into the antibody polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses antibodies which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4, acetylation, formylation, oxidation, reduction, metabolic synthesis in the presence of tunicamycin, etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The antibodies may also be modified with a detectable label, such as an enzymatic, fluorescent, radioisotopic or affinity label to allow for detection and isolation of the antibody.

Also provided by the invention are chemically modified derivatives of antibodies of the invention which may provide additional advantages such as increased solubility, stability and in vivo or in vitro circulating time of the polypeptide, or decreased immunogenicity (see, for example, U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The antibodies may be modified at random positions within the molecule, or at predetermined positions within the molecule and may include one, two, three or more attached chemical moieties.

The polymer may be of any molecular weight and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2560, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

In a preferred embodiment, antibodies of the invention preferentially bind GSS-eNOS, or fragments and variants thereof relative to their ability to bind other antigens. An antibody's ability to preferentially bind one antigen compared to another antigen may be determined using any method known in the art.

By way of non-limiting example, an antibody may be considered to bind a first antigen preferentially if it binds said first antigen with a dissociation constant ($K_D$) that is less than the antibody's $K_D$ for the second antigen. In another non-limiting embodiment, an antibody may be considered to bind a first antigen preferentially if it binds said first antigen with an affinity (i.e., $K_D$) that is at least one order of magnitude less than the antibody's $K_D$ for the second antigen. In another non-limiting embodiment, an antibody may be considered to bind a first antigen preferentially if it binds said first antigen with an affinity (i.e., $K_D$) that is at least two orders of magnitude less than the antibody's $K_D$ for the second antigen.

In another non-limiting embodiment, an antibody may be considered to bind a first antigen preferentially if it binds said first antigen with an off rate ($k_{off}$) that is less than the antibody's $k_{off}$ for the second antigen. In another non-limiting embodiment, an antibody may be considered to bind a first antigen preferentially if it binds said first antigen with a $k_{off}$ that is at least one order of magnitude less than the antibody's $k_{off}$ for the second antigen. In another non-limiting embodiment, an antibody may be considered to bind a first antigen preferentially if it binds said first antigen with a $k_{off}$ that is at least two orders of magnitude less than the antibody's $k_{off}$ for the second antigen.

The present invention further includes compositions comprising, or alternatively consisting of, heterologous polypeptides fused or conjugated to antibody fragments. For example, the heterologous polypeptides may be fused or conjugated to a Fab fragment, Fd fragment, Fv fragment, $F(ab)_2$ fragment, or a portion thereof. Methods for fusing or conjugating polypeptides to antibody portions are known in the art.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of antibodies (including molecules comprising, or alternatively consisting of, antibody fragments or variants thereof), such methods can be used to generate antibodies with altered activity (e.g., antibodies with higher affinities and lower dissociation rates).

The present invention further encompasses antibodies (including antibody fragments or variants thereof), conjugated to a diagnostic or therapeutic agent. The antibodies can be used, for example, as part of a clinical testing procedure to, e.g., determine the safety or efficacy of a given treatment regimen. Detection can be facilitated by coupling the antibody to a detectable substance. Examples of detectable substances include, but are not limited to, various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or indirectly, through an intermediate (such as, for example, a linker known in the art) using techniques known in the art. Examples of suitable enzymes include, but are not limited to, horseradish peroxidase, alkaline phosphatase, beta-galactosidase, or acetylcholinesterase; examples of suitable prosthetic group complexes include, but are not limited to, streptavidin/biotin and avidin/biotin; examples of suitable fluorescent materials include, but are not limited to, umbelliferone, fluorescein, fluorescein isothiocyanate, rhodamine, dichlorotriazinylamine fluorescein, dansyl chloride or phycoerythrin; an example of a luminescent material includes, but is not limited to, luminol; examples of bioluminescent materials include, but are not limited to, luciferase, luciferin, and acquorin; and known suitable radioactive materials.

Antibodies of the present invention may be used, for example, but not limited to, to purify, detect, and target redox modulated proteins, including both in vitro and in vivo diagnostic and therapeutic methods. For example, the antibodies have use in immunoassays for qualitatively and quantitatively measuring levels of redox modulated proteins in biological and non-biological samples.

One or more antibodies of the present invention (including molecules comprising, or alternatively consisting of, antibody fragments or variants thereof) that specifically bind to redox modulated proteins may be used locally or systemically in the body as a prophylactic or a therapeutic. The present invention is further directed to antibody-based therapies which involve administering antibodies of the invention (including molecules comprising, or alternatively consisting of, antibody fragments or variants thereof) to an animal, preferably a mammal, and most preferably a human, for treating individuals for diseases related to redox modulated proteins such as those diseases noted above.

Various delivery systems are known and can be used to administer antibody or fragment or variant thereof of the invention, e.g., encapsulation in liposomes, microparticles, microcapsules, recombinant cells capable of expressing the antibody or antibody fragment. Methods of introduction include, but are not limited to, intradermal, intramuscular, intraperitoneal, intravenous, subcutaneous, intranasal, epidural, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The present invention also provides pharmaceutical compositions. Such compositions comprise a therapeutically effective amount of an antibody or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin. Such compositions will contain a therapeutically effective amount of the antibody or fragment thereof, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration, are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. The present invention provides kits that can be used in the above methods. In one embodiment, a kit comprises an antibody of the invention, preferably a purified antibody, in one or more containers.

Examples

The following examples are included to demonstrate various embodiments of the present invention. It will be appreciated by those skilled in the art that the techniques disclosed in the examples which follow represent techniques discovered by the inventors to function well in practice. However, those of skill in the art should, in light of the present disclosure, appreciate that many changes can be made in the specific embodiments which are disclosed herein while still obtaining like or similar results without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention.

General Methods

Generally, nomenclatures utilized in connection with, and techniques of, cell and tissue culture, molecular biology, and protein and oligo- or polynucleotide chemistry and hybridization described herein are those known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. The nomenclatures utilized in connection with, and the laboratory procedures and techniques of described herein are those well-known and commonly used in the art. See, for example, *Antibodies: A Laboratory Manual*, Ed Harlow, David Lane (1988); (Cold Spring Harbor Press, 1988).

Antigen Preparation

Synthesis of Immunogen and Other Peptides:

The immunogen peptide shown in FIG. 2A (SEQ ID NO: 4) and the other biotinylated peptides of the present invention (see FIGS. 2B-2D/SEQ ID NOS: 5-7) were prepared using standard Fmoc/t-But chemistry and the cyclic peptide (FIG. 2B/SEQ ID NO: 5) was synthesized by a PEO-Maleimide reaction. The cyclic and linear peptides of this invention were further purified using semi-preparative RP-HPLC and characterized by electrospray ionization mass spectroscopy. Such techniques and assays are known to those of ordinary skill in the art.

One embodiment of this invention provides a first anti-glutathionylated eNOS antibody, wherein the anti-glutathionylated eNOS antibody has been generated against an immunogen consisting of a peptide that includes glutathione; a first linker, an eNOS peptide; a second linker, and a T-cell epitope (see FIG. 2A/SEQ ID NO: 4); and wherein the anti-glutathionylated eNOS antibody is adapted to recognize redox modulated eNOS proteins in animals, including mammals. Another embodiment of this invention provides a second isolated antibody. This second isolated antibody includes an anti-glutathionylated eNOS antibody, wherein the anti-glutathionylated eNOS antibody has been generated against an immunogen consisting of a peptide that includes glutathione; a first linker; an eNOS peptide; a second linker a T-cell epitope (see FIG. 2A/SEQ ID NO: 4; and wherein the anti-glutathionylated eNOS antibody is adapted to recognize redox modulated eNOS proteins in mammals and other animals, wherein the redox modulated protein is a glutathionylated protein.

Still another embodiment of this invention provides a method for generating an antibody that recognizes redox modulated protein in animals, including mammals. This antibody is an anti-glutathionylated eNOS antibody and the method for generating the antibody includes providing an immunogen consisting of a peptide that includes glutathione; a first linker, an eNOS peptide; a second linker, and a T-cell epitope (see FIG. 2A/SEQ ID NO: 4); immunizing a selected mammal with the immunogen; and isolating a monoclonal antibody using techniques and methods known to one of ordinary skill in the art (see description below). These techniques and methods include isolating antibody-producing cells taken from the immunized mammal; fusing the isolated antibody-producing cells with myeloma cells resulting in a hybridoma; cloning the hybridoma and recovering antibody from the culture thereof to yield a monoclonal antibody, and purifying the monoclonal antibodies using a glutathionylated peptide. FIG. 2A provides the amino acid sequence (SEQ ID NO: 4) for an immunogen peptide in accordance with an exemplary embodiment of the present invention, wherein the immunogen includes glutathione; Linker 1 (L1); eNOS 685-693; Linker 2 (L2); and measles virus fusion protein (MVF)/T-cell epitope; FIG. 2B provides the amino acid sequence (SEQ ID NO: 5) for a glutathionylated eNOS peptide (Gp); FIG. 2C provides the amino acid sequence (SEQ ID NO: 6) for a non-glutathionylated eNOS peptide (NGp); and FIG. 2D provides the amino acid sequence (SEQ ID NO: 7) for glutathione (GSH).

With regard to this invention, monoclonal antibody was prepared using established hybridoma methods, such as those described by Kohler and Milstein (1975); Nature 256:495. In the current method, mice were immunized with an immunogen (see FIG. 2A) to elicit an immune response therefrom. Mouse spleen cells were then fused with an immortal lymphoma cell line using a suitable fusing agent, such as polyethylene glycol to form a hybridoma cell (see Goding (1986); *Monoclonal Antibodies: Principles and Practice*, Academic Press, pp. 59-103). Immortalized cell lines may be transformed into mammalian cells. Hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high-level expression of antibody by the selected antibody-producing cells, and that are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. The culture medium in which the hybridoma cells are cultured can then be assayed for the presence of monoclonal antibodies directed against glutathionylated eNOS peptide (Gp, see FIG.

2B/SEQ ID NO: 5). The binding specificity of monoclonal antibodies produced by the hybridoma cells was determined by enzyme-linked immunoabsorbent assay (ELISA). Such techniques and assays are well known in the art. After the desired hybridoma cells are identified, the clones may be subcloned by limiting dilution procedures and grown by standard methods. Suitable culture media for this purpose include, for example, Dulbecco's Modified Eagle's Medium and RPMI-1640 medium. The monoclonal antibodies secreted by the subclones may be isolated or purified from the culture medium by protein G and affinity chromatography. Such techniques and assays are also well known in the art.

Enzyme-Linked Immunosorbent Assay (ELISA)

Pierce Streptavidin Coated or Nunc-Immuno MaxiSorb 96 well Plates were coated with 2 ug of immunogen or biotinylated peptide [glutathionylated eNOS (Gp) (FIG. 2B/SEQ ID NO: 5) or eNOS (NGp) (FIG. 2C/SEQ ID NO: 6) or glutathione (GSH) (FIG. 2D/SEQ ID NO: 7)—in 10 mM PBS buffer, pH 7.4. After blocking with 0.1% BSA (Sigma-Aldrich, MO) in PBS-Tween 20 (0.05%) at 37° C. for 2 hours, antibody or pre-immune serum control were added to the wells in 100 µl volume. The secondary antibody was peroxidase-conjugated goat anti-rabbit immunoglobulin (Millipore, Calif.) at 1/10000. TMB peroxidase substrate system solution (Millipore, Calif.) was added and color development was terminated after 4 minutes using 1M HCl. Absorbance at 450 nm was detected using a GENios pro plate reader (Tecan, N.C.).

Immunocytochemistry

Cells [Bovine Aortic Endothelial cells (BAECs), Human Aortic Endothelial cells (HAECs)] grown on sterile coverslips were treated/untreated with menadione for 1 hr, were fixed with 3.7% paraformaldehyde and permeabilized with 0.25% TritonX-100 in 1×PBS-BSA (0.01%). Non-specific binding was blocked with 10% normal goat serum (Vector Labs, CA.) for 1 hr and exposed to primary antibody (GeNOS, eNOS, or GSH) for 3 hours at 37° C., washed three times with IX PBS-BSA, incubated with secondary antibody [anti-mouse IgG-Alexa Flour 488, (Molecular probes, CA)]+Hoechst dye for 1 hour at 37° C., and again washed three times with IX PBS-BSA. Fluoromount-G (Southern Biotechnology) was used to attach coverslips to slides. Fluorescence was viewed using a confocal microscope equipped with epi-illuminescence.

Antibody Production

Phase I included immunization of mice and serum screening and required approximately 6-10 weeks. Immunization of four (4) mice (Balb/c) with antigen(s) was done to stimulate antibody production. ELISA was used to determine which mice exhibited the highest titer, and those mice were used for cell fusion. Approximately 2 mg of antigen was used for immunization. The immunogen may be provided as either a powder or in solution, although the immunogen must be soluble (no gel) for IV boosts at the end of a production schedule. A recommended concentration is ≥1 mg/ml (PBS). An additional 4 mg of antigen in liquid for plate coating was used for screening by ELISA. A screening strategy was developed prior to the initiation of a monoclonal experiment for assuring efficient detection of potentially useful hybridomas. Antibody-producing hybridomas were tested in the assay for which they were to be used (i.e., if antibodies are to be used in Western blots, such antibodies need to be screened by Western blots).

Phase II included fusion and screening of the hybridoma supernatant and required approximately 3-5 weeks. An antibody-producing mouse was selected for fusion of spleen cells with myeloma cells. Fusion product was distributed into several 96 well culture plates. Screening of all wells containing fusion products was assayed by ELISA utilizing the provided antigen(s). The antibody secreting wells (up to 48 positives) with the higher titer (as determined by OD measurement) were grown in 24-well plates and retested by ELISA. Up to eight positive wells were amplified and frozen for parental hybridomas.

Phase III included cloning and required approximately 4-6 weeks. Two of the most suitable hybridomas were selected and cloned by the limiting dilution method and screened by ELISA. Clones with the desired titer and specificity were expanded and the remaining antibody containing media (1 ml from up to 5 positive clones) from each of the sub-clones was evaluated. Positive clones with the highest titer (as determined by OD measurement) were temporarily frozen in duplicate vials for further analysis and selection of desired clones for re-cloning.

Phase III included re-cloning and required approximately 4-6 weeks. A selected clone was then re-cloned by limiting dilution technique and plated into five 96 well plates to generate a stable cell line. Growing cells were then screened for secretion of antigen specific antibody by ELISA. The media samples from up to 5 positive antibody-secreting clones (100-150 µl) were evaluated. Positive clones were transferred to a 24-well plate and kept in culture for 5 days, thereby allowing time for selection of a single clone for final expansion and subsequent cryopreservation. Ultimately, all 5 clones were expanded and temporarily frozen in duplicate vials, thereby allowing time for selecting the final clone(s) for expansion and cell storage.

FIGS. 3A-D are tables showing the ELISA immunoreactivity of antibodies secreted by hybridoma clones (1A9, 1C6, 1E7, 1E9, 1E10, 1G12, 2C10, 2E12, 2F8, 3C9, 3F1, 4B7, 4C10, 4E6, 4E12, 4G3, 5A2, 5F8, 6A4), Cardiac Serum (CarSer), pre-immune Naïve Serum (NaiSer), hybridoma culture media (Media) to positive control peptide (glutathionylated-eNOS peptide (FIG. 3A); negative control peptide (non-glutathionylated eNOS peptide)(FIG. 3B); glutathione (GSH)(FIG. 3C); and immunogen peptide (the immunogen peptide of FIG. 2A)(FIG. 3D).

FIGS. 4A-H are a series of photomicrographs that include immuno-staining and confocal images of purified 4C10, 4G3, 5F8, 6A4 clone antibodies and bovine aortic endothelial cells (BAEC) treated with menadione (25 uM), and without DTT (−DTT) or with DTT (+DTT, 100 uM), wherein a blue and green staining pattern indicates nuclei (stained with DAPI) and glutathionylated eNOS antibodies, wherein only the photomicrographs showing the staining of the 5F8 antibody demonstrate binding with GeNOS and removal with DTT treatment, and wherein other antibodies (4C10, 4G3) were either bound with cells and not removed by DTT treatment, or demonstrated only weak binding (6A4).

Figure 5A:
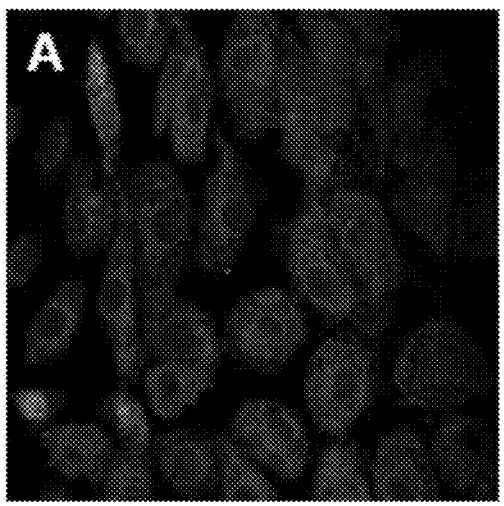
Figure 5B:
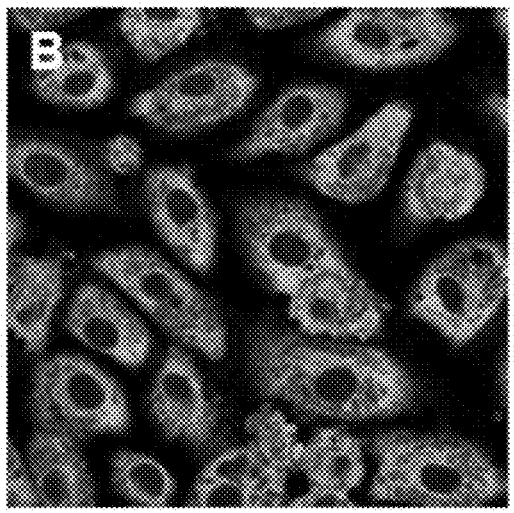
Figure 5C:
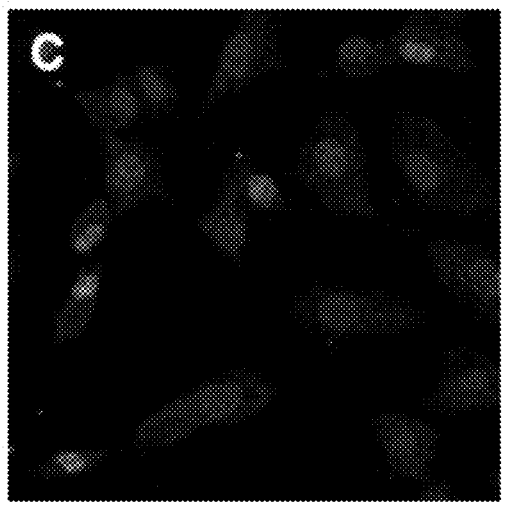
Figure 5D:
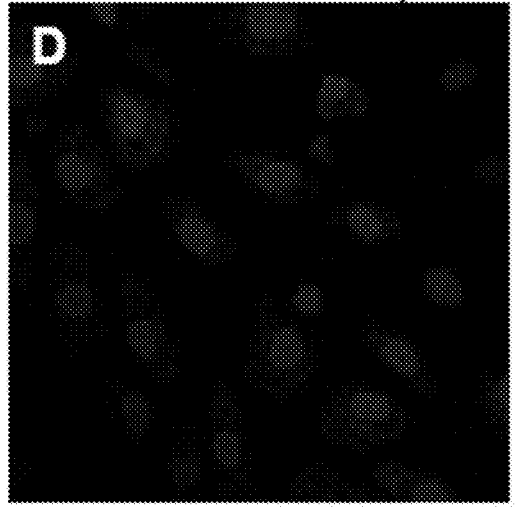

FIGS. 5A-D are a series of photomicrographs that include immuno-staining and confocal images of bovine aortic endothelial cells (BAEC), wherein FIG. 5A shows control cells not treated with diamide and DTT; wherein FIG. 5B B shows cells treated with diamide (25 uM) and without DTT treatment; wherein FIG. 5C shows cells treated with diamide (25 uM) and DTT (100 uM); wherein FIG. 5D shows cells treated with diamide (25 uM), not treated with DTT and pre-incubated with glutathionylated eNOS peptide (5 ug); and wherein antibody 5F8 pre-treated with 5 ug eNOS peptide (Glu-eNOSpep shown in FIG. 2B) did not bind with cellular (BAEC) GeNOS protein, thereby confirming specificity to GeNOS Antibody.

Figure 6A:
Figure 6B:
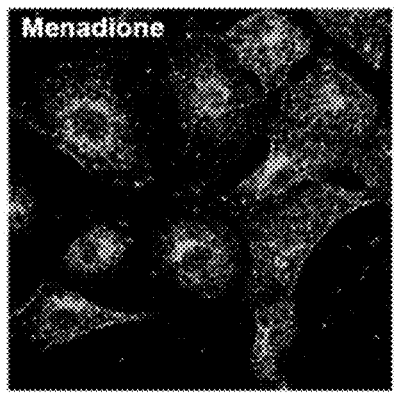
Figure 6C:
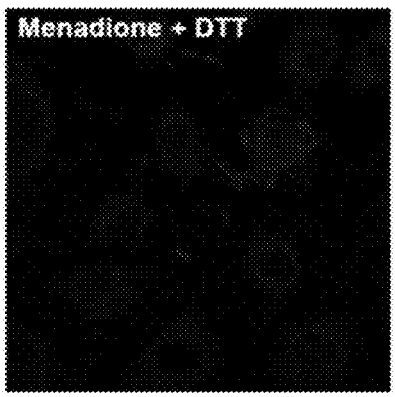
Figures 7A, 7B:
FIGS. 7A-D are a series of photomicrographs that include antibody 5F8 immunostaining and confocal images of HAECs clearly showing binding with GeNOS protein; wherein the glutathione antibody binds with all the glutathionylated proteins; and wherein the eNOS antibody shows the co-localization of the GeNOS antibody and confirms the 5F8 antibody is staining the same protein, but glutathionylated eNOS specifically.
Figures 7C, 7D:
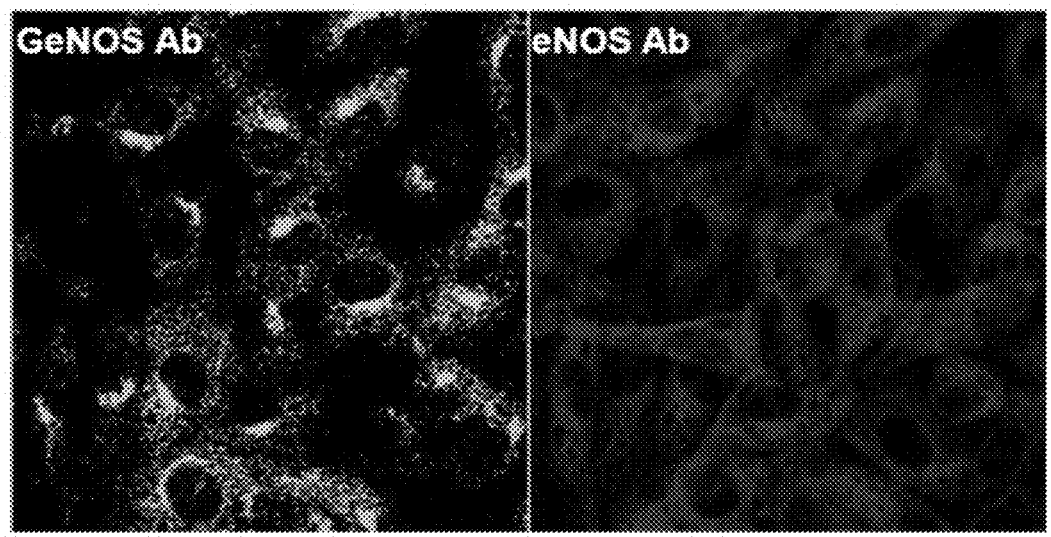

FIGS. 6A-C are a series of photomicrographs that include immunocytochemical localization and confocal microscopy of glutathionylated eNOS in human aortic endothelial cells (HAEC) treated with (40 uM) menadione or menadione (40 uM) and DTT (100 uM), wherein FIG. 6B shows the characteristic perinuclear/plasma membrane staining of GeNOS in HAECs treated with Menadione (40 uM) when compared to untreated cells (FIG. 6A) or menadione (40 uM) and DTT (100 uM) treated cells (FIG. 6C).

FIGS. 7A-D are a series of photomicrographs that include antibody 5F8 immunostaining and confocal images of HAECs clearly showing binding with GeNOS protein; wherein the glutathione antibody binds with all the glutathionylated proteins; and wherein the eNOS antibody shows the co-localization of the GeNOS antibody and confirms the 5F8 antibody is staining the same protein, but glutathionylated eNOS specifically.

While the present invention has been illustrated by the description of exemplary embodiments thereof, and while the embodiments have been described in certain detail, there is no intention to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described. Accordingly, departures may be made from such details without departing from the spirit or scope of the general inventive concept.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, and by way of example, a description of a technology in the "Background" is not to be construed as an admission that certain technology is prior art to any embodiment(s) in this disclosure. Neither is the "Summary" to be considered as an exhaustive characterization of the embodiment(s) set forth in issued claims. Furthermore, any reference in this disclosure to "invention" in the singular should not be used to argue that there is only a single point of novelty in this disclosure. Multiple embodiments may be set forth according to the limitations of the multiple claims issuing from this disclosure, and such claims accordingly define the embodiment(s), and their equivalents, that are protected thereby. In all instances, the scope of such claims shall be considered on their own merits in light of this disclosure but should not be constrained by the headings set forth herein.

What is claimed:

1. An isolated antibody, consisting of:
    (a) an anti-glutathionylated endothelial nitric oxide synthase (eNOS) antibody,
    (b) wherein the anti-glutathionylated eNOS antibody has been generated against an immunogen consisting of a peptide that includes glutathione; a first linker; an eNOS peptide; a second linker, and a T-cell epitope; and
    (c) wherein the anti-glutathionylated eNOS antibody is adapted to recognize redox modulated eNOS proteins.

2. The antibody of claim 1, wherein the recognized redox modulated eNOS proteins are glutathionylated proteins.

3. The antibody of claim 1, wherein the recognized redox modulated eNOS proteins occur in bovines, humans, rats, or mice.

4. The antibody of claim 1, wherein the immunogen has an amino acid sequence consisting of SEQ ID NO. 4.

5. The antibody of claim 1, wherein the T-cell epitope is a measles virus fusion protein.

6. An isolated antibody, consisting of:
    (a) an anti-glutathionylated eNOS antibody,
    (b) wherein the anti-glutathionylated eNOS antibody has been generated against an immunogen consisting of a peptide that includes glutathione; a first linker; an eNOS peptide; a second linker, a T-cell epitope, and that has an amino acid sequence consisting of SEQ ID NO. 4,
    (c) wherein the anti-glutathionylated eNOS antibody is adapted to recognize redox modulated eNOS proteins, and
    (d) wherein the recognized redox modulated proteins are glutathionylated proteins.

7. The antibody of claim 6, wherein the recognized redox modulated eNOS proteins occur in bovines, humans, rats, or mice.

8. The antibody of claim 6, wherein the T-cell epitope is a measles virus fusion protein.

9. A method for generating an antibody that recognizes redox modulated eNOS proteins, wherein the antibody is an anti-glutathionylated eNOS antibody, and wherein the method comprises:
    (a) providing an immunogen consisting of a peptide that includes glutathione; a first linker; an eNOS peptide; a second linker, and a T-cell epitope;
    (b) immunizing a selected mammal with the immunogen;
    (c) isolating the blood serum from the immunized mammal containing antibodies;
    (d) isolating antibody-producing cells taken from the spleen or lymph node of the immunized mammal;
    (e) fusing the isolated antibody-producing cells with myeloma cells resulting in a hybridoma;
    (f) cloning the hybridoma and recovering antibody from the culture thereof to yield a monoclonal antibody; and
    (g) purifying the monoclonal antibodies using a glutathionylated peptide.

10. The method of claim 9, wherein the recognized redox modulated eNOS proteins are glutathionylated proteins.

11. The method of claim 9, wherein the recognized redox modulated eNOS proteins occur in bovines, humans, rats, or mice.

12. The method of claim 9, wherein the T-cell epitope is a measles virus fusion protein.

13. The method of claim 9, wherein the immunogen has an amino acid sequence consisting of SEQ ID NO. 4.

* * * * *

SEQUENCE LISTING

```
<160> NUMBER OF SEQ ID NOS: 7

<210> SEQ ID NO 1
<211> LENGTH: 60
<212> TYPE: PRT
<213> ORGANISM: Artificial Sequence
<220> FEATURE:
<223> OTHER INFORMATION: Human Nitric Oxide Synthase - amino acids
      659-718

<400> SEQUENCE: 1

His Phe Cys Ala Phe Ala Arg Ala Val Asp Thr Arg Leu Glu Glu Leu
1               5                   10                  15

Gly Gly Glu Arg Leu Leu Gln Leu Gly Gln Gly Asp Glu Leu Cys Gly
            20                  25                  30

Gln Glu Glu Ala Phe Arg Gly Trp Ala Gln Ala Ala Phe Gln Ala Ala
        35                  40                  45

Cys Glu Thr Phe Cys Val Gly Glu Asp Ala Lys Ala
    50                  55                  60

<210> SEQ ID NO 2
<211> LENGTH: 60
<212> TYPE: PRT
<213> ORGANISM: Artificial Sequence
<220> FEATURE:
<223> OTHER INFORMATION: Rat Nitric Oxide Synthase - amino acids 658-717

<400> SEQUENCE: 2

His Phe Cys Ala Phe Ala Arg Ala Val Asp Thr Arg Leu Glu Glu Leu
1               5                   10                  15

Gly Gly Glu Arg Leu Leu Gln Leu Gly Gln Gly Asp Glu Leu Cys Gly
            20                  25                  30

Gln Glu Glu Ala Phe Arg Gly Trp Ala Gln Ala Ala Phe Gln Ala Ala
        35                  40                  45
```

```
Cys Glu Thr Phe Cys Val Gly Glu Asp Ala Lys Ala
     50                  55                  60

<210> SEQ ID NO 3
<211> LENGTH: 60
<212> TYPE: PRT
<213> ORGANISM: Artificial Sequence
<220> FEATURE:
<223> OTHER INFORMATION: Mouse Nitric Oxide Synthase - amino acids
      658-717

<400> SEQUENCE: 3

His Phe Cys Ala Phe Ala Arg Ala Val Asp Thr Arg Leu Glu Glu Leu
1               5                   10                  15

Gly Gly Glu Arg Leu Leu Gln Leu Gly Gln Gly Asp Glu Leu Cys Gly
            20                  25                  30

Gln Glu Glu Ala Phe Arg Gly Trp Ala Gln Ala Ala Phe Gln Ala Ala
        35                  40                  45

Cys Glu Thr Phe Cys Val Gly Glu Asp Ala Lys Ala
     50                  55                  60

<210> SEQ ID NO 4
<211> LENGTH: 40
<212> TYPE: PRT
<213> ORGANISM: Artificial Sequence
<220> FEATURE:
<223> OTHER INFORMATION: Immunogen

<400> SEQUENCE: 4

Gly Cys Glu Gly Pro Ser Leu Ser Ser Gly Asp Glu Leu Cys Gly Gln
1               5                   10                  15

Glu Glu Gly Pro Ser Leu Lys Leu Leu Ser Leu Ile Lys Gly Val Ile
            20                  25                  30

Val His Arg Leu Glu Gly Val Glu
        35                  40

<210> SEQ ID NO 5
<211> LENGTH: 12
<212> TYPE: PRT
<213> ORGANISM: Artificial Sequence
<220> FEATURE:
<223> OTHER INFORMATION: Glutathionylated eNOS peptide

<400> SEQUENCE: 5

Gly Asp Glu Leu Cys Gly Cys Glu Gly Gln Glu Glu
1               5                   10

<210> SEQ ID NO 6
<211> LENGTH: 9
<212> TYPE: PRT
<213> ORGANISM: Artificial Sequence
<220> FEATURE:
<223> OTHER INFORMATION: NGP

<400> SEQUENCE: 6

Gly Asp Glu Leu Cys Gly Gln Glu Glu
1               5

<210> SEQ ID NO 7
<211> LENGTH: 3
<212> TYPE: PRT
<213> ORGANISM: Artificial Sequence
<220> FEATURE:
<223> OTHER INFORMATION: GSH
```

```
<400> SEQUENCE: 7

Gly Cys Glu
1
```